United States Patent
Oba et al.

(10) Patent No.: US 10,585,061 B2
(45) Date of Patent: Mar. 10, 2020

(54) GAS SENSOR AND METHOD FOR MANUFACTURING THE SAME

(71) Applicant: NGK Spark Plug Co., LTD., Nagoya (JP)

(72) Inventors: Takehiro Oba, Konan (JP); Shogo Nagata, Komaki (JP); Shunya Mihara, Komaki (JP)

(73) Assignee: NGK Spark Plug Co., LTD., Nagoya (JP)

( * ) Notice: Subject to any disclaimer, the term of this patent is extended or adjusted under 35 U.S.C. 154(b) by 191 days.

(21) Appl. No.: 15/642,153

(22) Filed: Jul. 5, 2017

(65) Prior Publication Data

US 2018/0011048 A1 Jan. 11, 2018

(30) Foreign Application Priority Data

Jul. 7, 2016 (JP) .................. 2016-135100
Jun. 30, 2017 (JP) .................. 2017-128370

(51) Int. Cl.

| | |
|---|---|
| *G01N 27/406* | (2006.01) |
| *G01N 27/407* | (2006.01) |
| *H01R 4/18* | (2006.01) |
| *H01R 13/26* | (2006.01) |
| *H01R 43/048* | (2006.01) |
| *H01R 43/20* | (2006.01) |
| *H01R 13/703* | (2006.01) |
| *H01R 13/05* | (2006.01) |

(52) U.S. Cl.
CPC ..... *G01N 27/4062* (2013.01); *G01N 27/4067* (2013.01); *G01N 27/4077* (2013.01); *H01R 4/184* (2013.01); *H01R 13/26* (2013.01); *H01R 43/048* (2013.01); *H01R 43/20* (2013.01); *H01R 13/05* (2013.01); *H01R 13/7033* (2013.01)

(58) Field of Classification Search
CPC ........... G01N 27/4062; G01N 27/4077; G01N 27/4067; H01R 4/184; H01R 13/26; H01R 43/20; H01R 43/048
See application file for complete search history.

(56) References Cited

U.S. PATENT DOCUMENTS

2010/0139379 A1* 6/2010 Kume ................ G01N 27/4062
73/114.73
2014/0299469 A1 10/2014 Oba et al.

FOREIGN PATENT DOCUMENTS

JP 2015-129727 A 7/2015

* cited by examiner

*Primary Examiner* — Louis J Rufo
(74) *Attorney, Agent, or Firm* — Leason Ellis LLP

(57) ABSTRACT

A gas sensor includes a sensing element that includes an electrode pad, a metal terminal, and a separator. The metal terminal includes a lead-wire-connecting portion, a main body, a protruding piece that protrudes from a front-end side, and an elastic portion connected to an end of the protruding piece and to the electrode pad. An area S1 of a first opposed surface of a primary surface facing an insertion hole of the separator is larger than an area S2 of a second opposed surface of a secondary surface facing the insertion hole, and a part of the second opposed surface contacts an inner circumferential surface of the separator forming the insertion hole, and the first opposed surface is separated from the inner circumferential surface, where surfaces of the main body and the protruding piece that are located opposite the elastic portion are the primary surface and the secondary surface.

7 Claims, 16 Drawing Sheets

FIG. 16
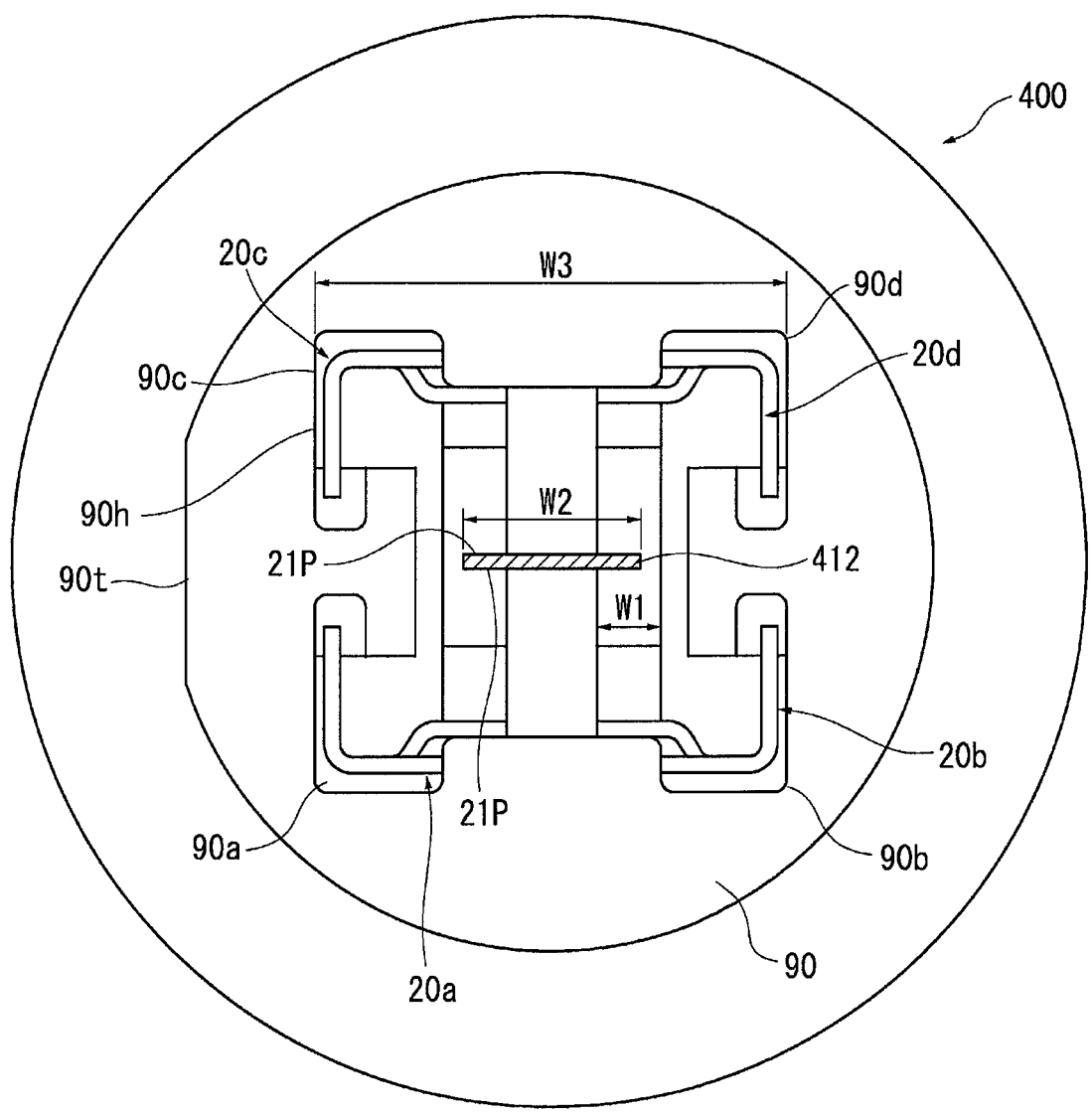
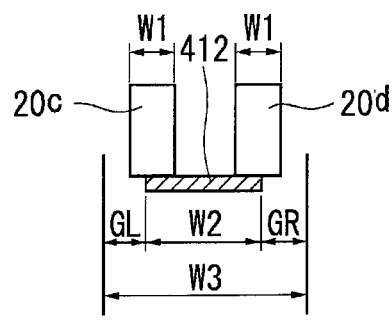

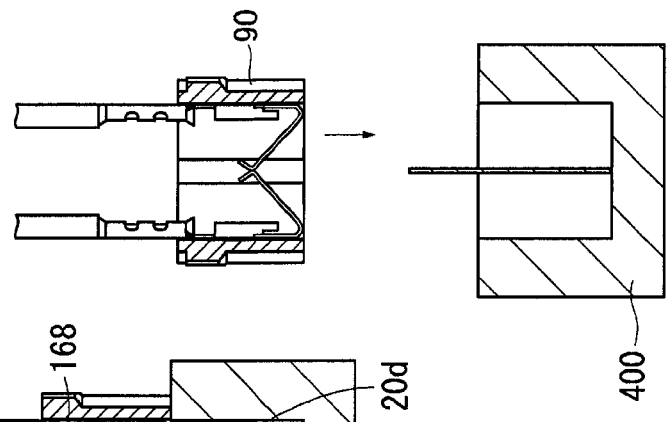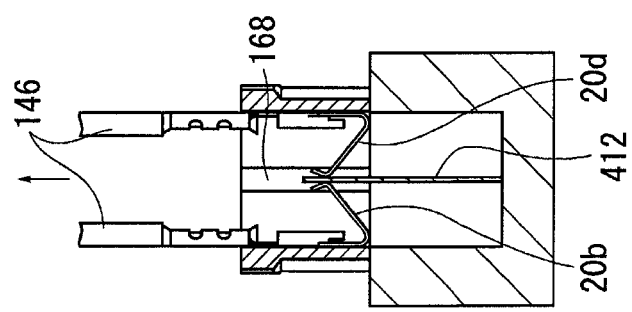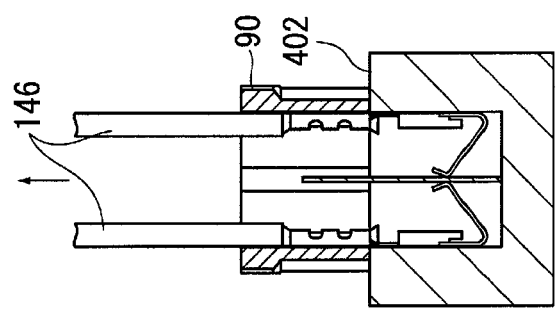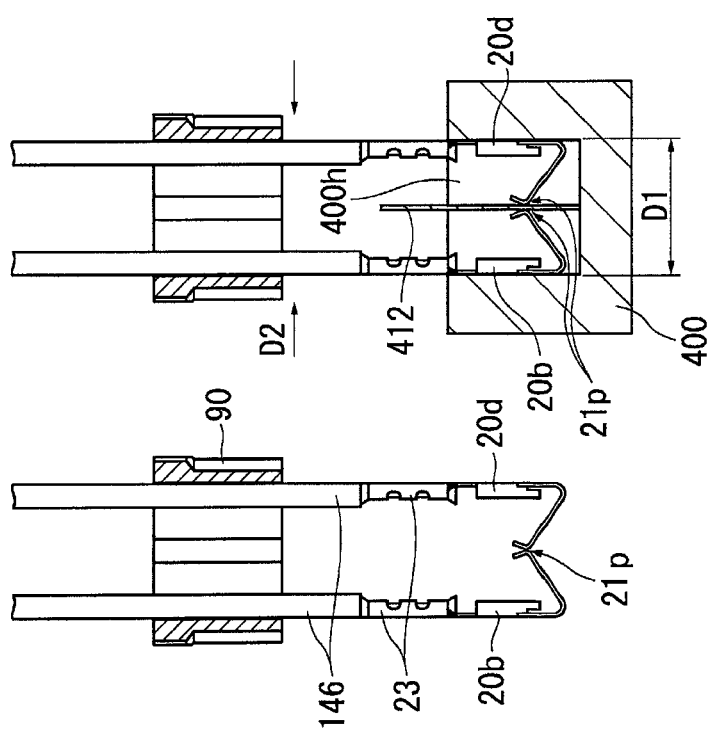

GAS SENSOR AND METHOD FOR MANUFACTURING THE SAME

This application claims the benefit of Japanese Patent Applications No. 2016-135100, filed Jul. 7, 2016 and No. 2017-128370, filed Jun. 30, 2017, both of which are incorporated herein by reference in their entireties

FIELD OF THE INVENTION

The present invention relates to a gas sensor including a sensing element that detects the concentration of a gas to be detected and a method for manufacturing the gas sensor.

BACKGROUND OF THE INVENTION

A known gas sensor that detects the concentration of oxygen or NOx in an exhaust gas of, for example, an automobile includes a plate-shaped sensing element that uses a solid electrolyte.

This type of gas sensor, which is widely used, includes electrode pads disposed on a rear-end-side outer surface of the plate-shaped sensing element, metal terminals are in electrical contact with the respective electrode pads to output a sensor output signal from the sensing element to the outside, and power is supplied to a heater stacked on the sensing element (Japanese Unexamined Patent Application Publication No. 2015-129727 (FIG. 5)).

As illustrated in FIG. 19, a metal terminal 200 has a U-shaped section formed of strips, for example, in a manner in which a metallic plate is cut and raised, and a part thereof on a front-end side of a primary surface 200a is folded toward the sensing element (not illustrated) and forms a folded portion 202 that is elastically connected to one of the electrode pads of the sensing element. A crimping portion 204 for crimping an end of a lead wire is formed on the rear-end side of the metal terminal 200. The metal terminal 200 itself is inserted and held in an insertion hole 1300h of a ceramic separator 1300.

Technical Problem

When the folded portion 202 comes into contact with the electrode pad of the sensing element, a reaction force F is applied from the electrode pad to the outside in the radial direction. Accordingly, it is necessary for the primary surface 200a of the metal terminal 200 to be in firm surface contact with the wall surface of the insertion hole 1300h of the separator 1300 to withstand the reaction force F.

However, in some cases where the separator 1300 is exposed to, for example, an exhaust gas and heated to a high temperature, heat is transferred to the metal terminal 200 from the separator 1300 via the primary surface 200a, and the metal terminal 200 is also heated to a high temperature. In this case, there is a risk that the folded portion 202 of the metal terminal 200 is softened and creep-deformed, elasticity thereof decreases, and reliability of the electrical connection with the sensing element decreases.

In view of this, it is an object of the present invention to provide a gas sensor that suppresses a decrease in the elasticity of the metal terminal due to heat transfer from the separator and that enables the electrode pad of the sensing element and the metal terminal to be electrically connected to each other with certainty, and a method for manufacturing the gas sensor.

SUMMARY OF THE INVENTION

Solution to Problem

To solve the above problems, a gas sensor according to the present invention includes a sensing element that is formed in a plate shape extending in a direction of an axial line and that includes an electrode pad on an outer surface of a rear-end side of the sensing element, a metal terminal that extends in the direction of the axial line and that is electrically connected to the electrode pad, a tubular separator that has an insertion hole in which the metal terminal is held and that surrounds a part of the sensing element on the rear-end side, and a lead wire that is connected to a rear-end side of the metal terminal and is pulled out to a rear-end side of the separator. The metal terminal includes a lead-wire-connecting portion that is connected to the lead wire, a main body that is connected to the lead-wire-connecting portion on a front-end side and that extends in the direction of the axial line, a protruding piece that protrudes from a front-end side of the main body in a direction intersecting the direction of the axial line, an elastic portion that is connected to an end of the protruding piece, that is folded toward the sensing element, and that is elastically connected to the electrode pad, a primary surface that is provided on the main body, located opposite the elastic portion and has a first opposed surface facing the insertion hole, and a secondary surface that is provided on the protruding piece, located opposite the elastic portion and has a second opposed surface facing the insertion hole. In the gas sensor, S1 is larger than S2, where S1 is an area of the first opposed surface and S2 is an area of the second opposed surface, at least a part of the second opposed surface is in contact with an inner circumferential surface of the separator forming the insertion hole, and the first opposed surface is separated from the inner circumferential surface of the insertion hole.

In this gas sensor, at least a part of the second opposed surface is in contact with (the wall surface of) the insertion hole, and, when a reaction force F is applied from the electrode pad of the sensing element outward in the radial direction, a folded portion facing the second opposed surface can properly withstand the reaction force. Consequently, the elastic force of the folded portion is maintained, and the electrode pad and the metal terminal can be electrically connected to each other in a stable manner.

Since the area S2 is smaller than the area S1, the area of the second opposed surface, which is likely to be exposed to heat from the separator because a portion having a part of the area S2 or the entire area S2 is in contact with (the wall surface of) the insertion hole or approaches (the wall surface of) the insertion hole more than the first opposed surface, is relatively decreased, and heat transfer from the separator to the entire metal terminal can be reduced. The entire second opposed surface may be in contact with the inner circumferential surface of the insertion hole (inner circumferential surface of the separator).

Since the first opposed surface, which has a large area, is separated from the insertion hole (inner circumferential surface of the separator), the first opposed surface, which has an area larger than the area of the second opposed surface and is separated from (the wall surface of) the insertion hole more than the second opposed surface, can be thermally insulated from the separator with air. Consequently, heat transfer from the separator to the entire metal terminal can be reduced.

Thus, the folded portion of the metal terminal is inhibited from being softened and creep-deformed due to heat transfer from the separator, the elasticity thereof is inhibited from decreasing, and the electrode pad of the sensing element and the metal terminal can be electrically connected to each other with certainty.

In the gas sensor according to the present invention, a minimum distance d1 between the first opposed surface and the insertion hole may be longer than a maximum distance d2 between the second opposed surface and the insertion hole.

In this gas sensor, the first opposed surface, which has an area larger than the area of the second opposed surface, is separated from (the wall surface of) the insertion hole more than the second opposed surface with certainty and can be thermally insulated from the separator with air. Consequently, heat transfer from the separator to the entire metal terminal can be further reduced.

According to an aspect of this gas sensor, the second opposed surface has the maximum distance d2, that is, the entire second opposed surface is not contact with (the wall surface of) the insertion hole, and a part of the second opposed surface is in contact with (the wall surface of) the insertion hole.

In the gas sensor according to the present invention, a part of the insertion hole facing the primary surface may be located further out in a radial direction than a part of the insertion hole facing the secondary surface.

In this gas sensor, the distance between the insertion hole and the primary surface can be increased, and heat transfer from the separator to the entire metal terminal can be further reduced.

In the gas sensor according to the present invention, the primary surface may be located further in, in a radial direction than the secondary surface.

In this gas sensor, the distance between the insertion hole and the primary surface can be increased, and heat transfer from the separator to the entire metal terminal can be further reduced.

In the gas sensor according to the present invention, a first stepped portion may be formed between the part of the insertion hole facing the primary surface and the part of the insertion hole facing the secondary surface. The secondary surface of the metal terminal may be connected to the primary surface with a second stepped portion interposed therebetween, and the primary surface is located further out in the radial direction than the secondary surface. The primary surface or the second stepped portion may be configured to position the metal terminal by engaging the first stepped portion.

In this gas sensor, since a part of the insertion hole facing the primary surface is located further out in a radial direction than a part of the insertion hole facing the secondary surface, the distance between the insertion hole and the primary surface can be increased. The first stepped portion is also used to set the position of the metal terminal. Accordingly, it is not necessary to provide the separator with a member for positioning of the metal terminal, and the shape of the separator is not complex, which improves productivity.

A method according to a first aspect of the present invention for manufacturing the gas sensor is a method for manufacturing the above gas sensor. The sensing element includes one or more pairs of the electrode pads on a front surface and a back surface. One or more pairs of the metal terminals have contact portions electrically connected to the corresponding electrode pads on the corresponding elastic portions while interposing the sensing element. The one or more pairs of the metal terminals are held in the insertion hole of the separator such that the contact portions face each other. The method includes a separator accommodating step of accommodating the separator from a rear-end side of a first jig and inserting a planar portion to a position corresponding to opposed surfaces in the insertion hole of the separator by using the first jig that has an accommodating space in which the separator is accommodated in the direction of the axial line and the planar portion having a predetermined thickness that is disposed at the position corresponding to the opposed surfaces of the contact portions and that extends along a part of the separator on the rear-end side from a bottom surface of the accommodating space when the separator and the metal terminals are accommodated in the accommodating space, a metal-terminal holding step of inserting the metal terminals into the insertion hole from the rear-end side of the separator and holding the metal terminals such that the planar portion is interposed between the contact portions, and a jig removing step of relatively removing the first jig from the separator to the front-end side.

In the method according to the first aspect for manufacturing the gas sensor, when one or more pairs of the metal terminals are installed in the separator such that the contact portions face each other, the planar portion of the first jig is interposed between the contact portions. Accordingly, the metal terminals that face each other are inhibited from coming into contact and being entangled with each other, the metal terminals are inhibited from being damaged and deformed, and workability can be improved.

A method according to a second aspect of the present invention for manufacturing the gas sensor is a method for manufacturing the gas sensor. The sensing element includes one or more pairs of the electrode pads on a front surface and a back surface. One or more pairs of the metal terminals have contact portions electrically connected to the corresponding electrode pads on the corresponding elastic portions while interposing the sensing element. The one or more pairs of the metal terminals are held in the insertion hole of the separator such that the contact portions face each other. The method includes a lead-wire inserting step of inserting lead wires to be connected to the respective metal terminals into the insertion hole of the separator such that the lead wires protrude from a front-end side of the insertion hole, a metal-terminal connecting step of electrically connecting the metal terminals to ends of the lead wires, a metal-terminal accommodating step of accommodating the metal terminals from a rear-end side of a second jig such that a planar portion is interposed between the contact portions by using the second jig that has an accommodating space whose inner diameter is equal to or smaller than a maximum outer diameter of an end portion of the separator and in which the metal terminals are accommodated in the direction of the axial line at the same positions as positions of the metal terminals to be held in the separator and the planar portion having a predetermined thickness that is disposed at a position corresponding to opposed surfaces of the contact portions and that extends in the direction of the axial line from a bottom surface of the accommodating space when the metal terminals are accommodated in the accommodating space, a separator contacting step of bringing an end of the separator into contact with a rear end of the second jig while pulling the lead wires toward the rear-end side, a metal-terminal holding step of inserting the metal terminals into the insertion hole from the front-end side of the insertion hole of the separator in contact with the rear end of the second jig to hold the metal terminals, and a jig removing step of relatively removing the second jig from the separator to the front-end side.

In the method according to the second aspect for manufacturing the gas sensor, when one or more pairs of the metal terminals are installed in the separator such that the contact portions face each other, the planar portion of the second jig is interposed between the contact portions. Accordingly, the metal terminals that face each other are inhibited from coming into contact and being entangled with each other, the metal terminals are inhibited from being damaged and deformed, and workability can be improved.

Advantageous Effects of Invention

The present invention can obtain a gas sensor that suppresses a decrease in the elasticity of the metal terminal due to heat transfer from the separator and that enables the electrode pad of the sensing element and the metal terminal to be electrically connected to each other with certainty.

BRIEF DESCRIPTION OF THE DRAWINGS

These and other features and advantages of the present invention will become more readily appreciated when considered in connection with the following detailed description and appended drawings, wherein like designations denote like elements in the various views, and wherein:

FIG. 16 illustrates a state where the metal terminals are accommodated in the second jig.

FIGS. 17A-17E are process drawings of a method according to the second aspect of the embodiment for manufacturing the gas sensor.

DETAILED DESCRIPTION OF THE INVENTION

Embodiments of the present invention will hereinafter be described.

Figure 1:
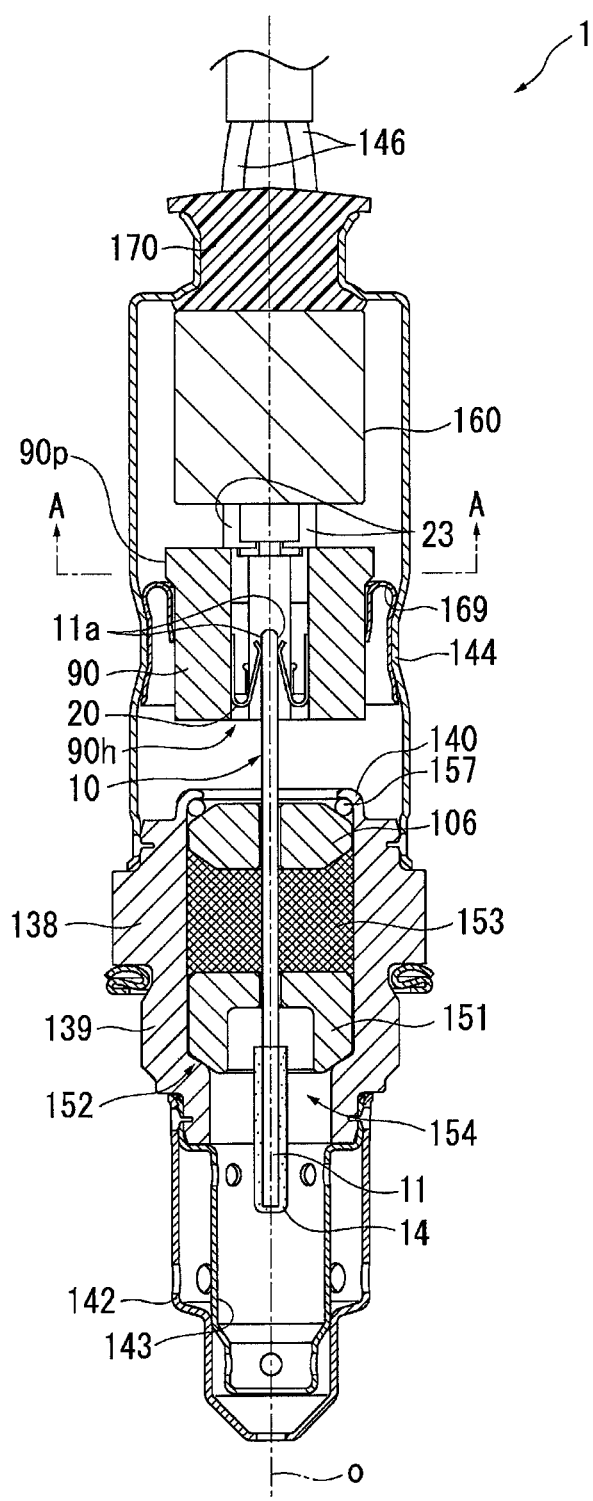
FIG. 1 is a sectional view of a gas sensor according to a first embodiment of the present invention in a direction of an axial line.
Figure 2:
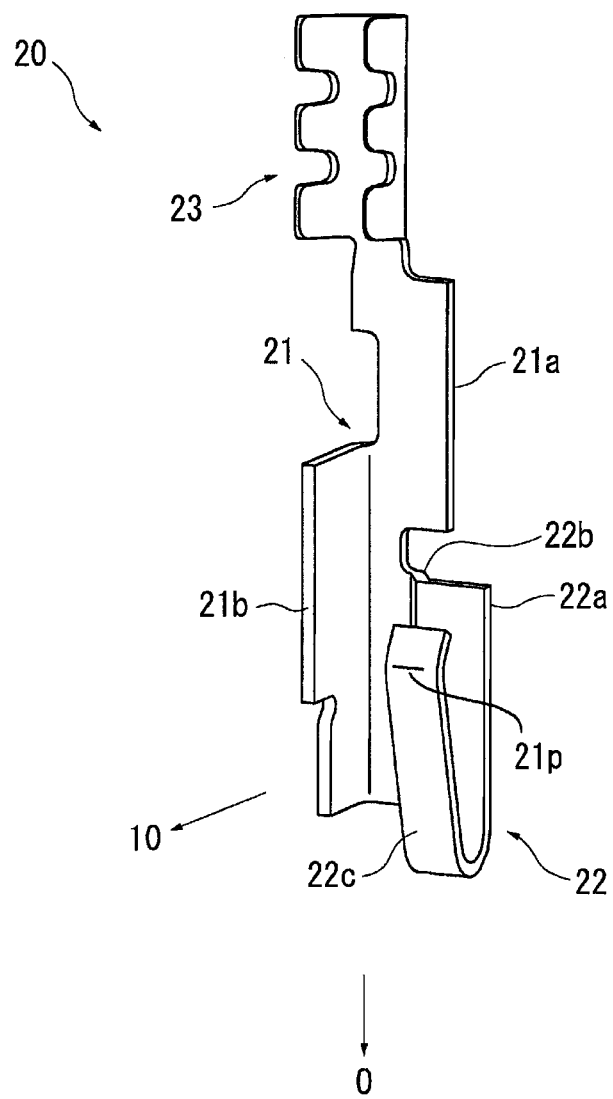
FIG. 2 is a perspective view of one of metal terminals according to the first embodiment.
Figure 3:
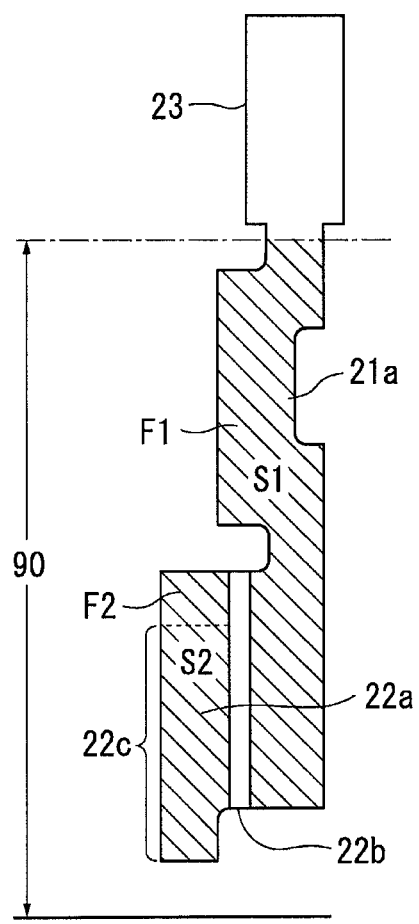
FIG. 3 is a rear view of the metal terminal according to the first embodiment.
Figure 4:
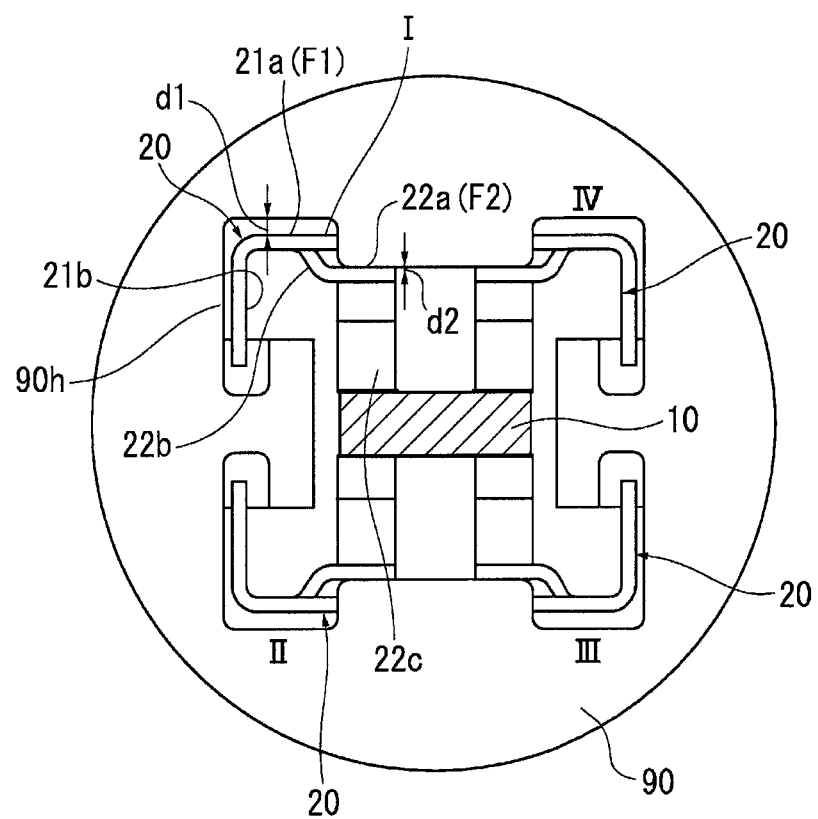
FIG. 4 is a sectional diagram illustrating a state where the metal terminals according to the first embodiment are inserted and held in insertion holes of a separator.

FIG. 1 is a full sectional view of a gas sensor (oxygen sensor) 1 according to a first embodiment of the present invention in a direction of an axial line O. FIG. 2 is a perspective view of one of metal terminals 20. FIG. 3 is a rear view of the metal terminal 20. FIG. 4 is a sectional diagram illustrating a state where the metal terminals 20 are inserted and held in insertion holes 90h of a first separator 90. FIG. 4 illustrates a section that is along line A-A in FIG. 1 and that is perpendicular to the direction of the axial line O.

The gas sensor 1 is an oxygen sensor that detects oxygen concentration in an exhaust gas of an automobile or various internal combustion engines.

In FIG. 1, the gas sensor 1 includes a tubular metal shell 138 including a screw portion 139 used to be secured to an exhaust pipe and formed on an outer surface, a plate-shaped sensing element 10 extending in the direction of the axial line O (the longitudinal direction of the gas sensor 1 or the vertical direction in the figure), a tubular ceramic sleeve 106 disposed such that the ceramic sleeve 106 surrounds the sensing element 10 in the radial direction, the first separator 90 that is formed of a ceramic tube and that is disposed in an interior space on the front-end side thereof such that the first separator 90 surrounds a rear-end portion of the sensing element 10, and four metal terminals 20 (only two metal terminals are illustrated in FIG. 1) that are inserted and held in the insertion holes 90h extending through the first separator 90 in the direction of the axial line O.

A second separator 160 that is formed of a ceramic tube is disposed on and in contact with the first separator 90 on the rear-end side, as described later.

The first separator 90 corresponds to a "separator" in the CLAIMS.

The four insertion holes 90h of the first separator 90 are in communication with the interior space on the front-end side of the first separator 90. The metal terminals 20 face the outer surface of the sensing element 10 on the rear-end side and are electrically connected to electrode pads 11a, 11b, 12a, 12b formed on the outer surface.

Two of the electrode pads 11a, 11b and 12a, 12b are arranged in the width direction on both surfaces of the sensing element 10 on the rear-end side. The electrode pads 11a, 11b, 12a, 12b can be formed, for example, as sintered bodies mainly formed of Pt.

A gas-detecting portion 11 at an end of the sensing element 10 is coated with a porous protective coat 14 such as alumina.

The metal shell 138 is composed of stainless steel, has a through-hole 154 extending in the direction of the axial line, and is formed in a substantially tubular shape having a ledge 152 protruding toward the inside of the through-hole 154 in the radial direction. The sensing element 10 is disposed in the through-hole 154 such that an end portion of the sensing element 10 protrudes from an end thereof. The ledge 152 is formed so as to have a tapered surface inclined inward with respect to a plane perpendicular to the direction of the axial line.

Inside the through-hole 154 of the metal shell 138, an alumina ceramic holder 151 having a substantially annular shape, a powder-filled layer 153 (also referred to below as a talc ring 153), and the ceramic sleeve 106 are stacked in this order from the front-end side to the rear-end side in a state where the sensing element 10 is surrounded in the radial direction.

A sheet packing 157 is disposed between the ceramic sleeve 106 and a rear-end portion 140 of the metal shell 138. The rear-end portion 140 of the metal shell 138 is crimped so as to press the ceramic sleeve 106 toward the front-end side with the sheet packing 157 interposed therebetween.

As illustrated in FIG. 1, an outer protector 142 and an inner protector 143, as a metallic (for example, stainless steel) double protector, which cover the protruding portion of the sensing element 10 and have holes, are installed on the outer circumference of the metal shell 138 on the front-end side (lower side in FIG. 1) by, for example, welding.

A metal pipe 144 is secured to the outer circumference of the metal shell 138 on the rear-end side. A rubber grommet 170, which has a lead-wire insertion hole (not illustrated) in which four lead wires 146 (only two lead wires are illustrated in FIG. 1) electrically connected to the four metal terminals 20 (only two metal terminals are illustrated in FIG. 1) of the sensing element 10 are inserted, is disposed in an opening of the metal pipe 144 on the rear-end side (upper side in FIG. 1).

The lead wires 146 are pulled from the rear-end side of the metal terminals 20 toward the rear-end side of the first separator 90, extend through an insertion hole (not illustrated) of the second separator 160 and the grommet 170, and are pulled to the outside of the gas sensor 1.

The first separator 90 is disposed on the rear-end side (upper side in FIG. 1) of the sensing element 10 protruding from the rear-end portion 140 of the metal shell 138, and a flange portion 90p protruding from an outer surface outward in the radial direction is provided. The first separator 90 is held inside the metal pipe 144 in a manner in which the flange portion 90p is in contact with the metal pipe 144 with a holding member 169 interposed therebetween.

The second separator 160 is disposed between the grommet 170 and the first separator 90. The second separator 160 presses the first separator 90 toward the front-end side by using an elastic force of the grommet 170. Thus, the flange portion 90p is pressed against the holding member 169, and the first separator 90 and the second separator 160 are held inside the metal pipe 144.

FIG. 2 is a perspective view of one of the metal terminals 20. According to the present embodiment, the gas sensor 1 includes the four metal terminals 20. As illustrated in FIG. 4, regarding the four metal terminals 20, the metal terminals 20 adjacent to each other in the first separator 90 are symmetric with each other with respect to a line, and accordingly, one of the metal terminals 20 (at a position I on the upper left side in FIG. 4) is described.

The metal terminal 20 on the lower left side at a position II in FIG. 4 is symmetric with the metal terminal 20 at the position I with respect to a line extending in the direction along a surface of the sensing element 10. The metal terminal 20 on the lower right side at a position III in FIG. 4 is symmetric with the metal terminal 20 at the position II with respect to a line perpendicular to the direction along a surface of the sensing element 10. The metal terminal 20 on the upper right side at a position IV in FIG. 4 is symmetric with the metal terminal 20 at the position I with respect to the line perpendicular to the direction along a surface of the sensing element 10.

As illustrated in FIG. 2, each of the metal terminals 20 extends in the direction of the axial line O as a whole and includes a lead-wire-connecting portion 23 that is connected to the corresponding lead wire 146 (see FIG. 1), a main body 21 that is connected to the lead-wire-connecting portion 23 on the front-end side and that extends in the direction of the axial line O, a protruding piece 22 that protrudes from the front-end side of the main body 21 in a direction (width direction in FIG. 1) intersecting the direction of the axial line O, and an elastic portion 22c that is connected to an end of the protruding piece 22, that is folded toward the sensing element 10, and that is elastically connected to one of the electrode pads, which are integrally formed. A protrusion of the elastic portion 22c that is in direct contact with the electrode pad is a contact portion 21p.

A surface of the main body 21 located opposite the elastic portion 22c is a primary surface 21a. A surface of the protruding piece 22 located opposite the elastic portion 22c is a secondary surface 22a.

The metal terminals 20 can be manufactured, for example, in a manner in which a metallic plate (Inconel (registered trademark), for example) is punched and subsequently folded into a predetermined shape, but are not limited thereto.

The lead-wire-connecting portion 23 is a known tubular press-fit terminal. A part of the lead wire 146 at which a covering is removed and a conducting wire is exposed is inserted into the tube and press-fitted, so that the lead wire 146 is electrically connected thereto.

The main body 21 has an L-shaped section and includes a guide portion 21b formed in a manner in which a portion outside the primary surface 21a in the width direction (opposite the secondary surface 22a) is folded at 90 degrees. The lead-wire-connecting portion 23 is integrally connected to the primary surface 21a on the rear-end side. Accordingly, the guide portion 21b, which corresponds to a surface of the main body 21 that is not connected to the lead-wire-connecting portion 23, does not correspond to the "primary surface". The guide portion 21b serves as a guide when the metal terminals 20 are inserted in the insertion holes 90h of the first separator 90. The main body 21 serves as a base portion of each metal terminal 20 and maintains the strength of the metal terminal 20.

Another portion outside the primary surface 21a in the width direction (opposite the guide portion 21b) is folded in the same direction as the guide portion 21b and forms a joint 22b integrally connected to the secondary surface 22a. The secondary surface 22a is parallel to the primary surface 21a. The protruding piece 22 includes the elastic portion 22c that is folded from an end of the secondary surface 22a toward the sensing element 10 and the rear-end side and that is elastically connected to an electrode pad 11a (see FIG. 1 and FIG. 9). The elastic portion 22c elastically bends in the radial direction with respect to the secondary surface 22a.

Figure 9:
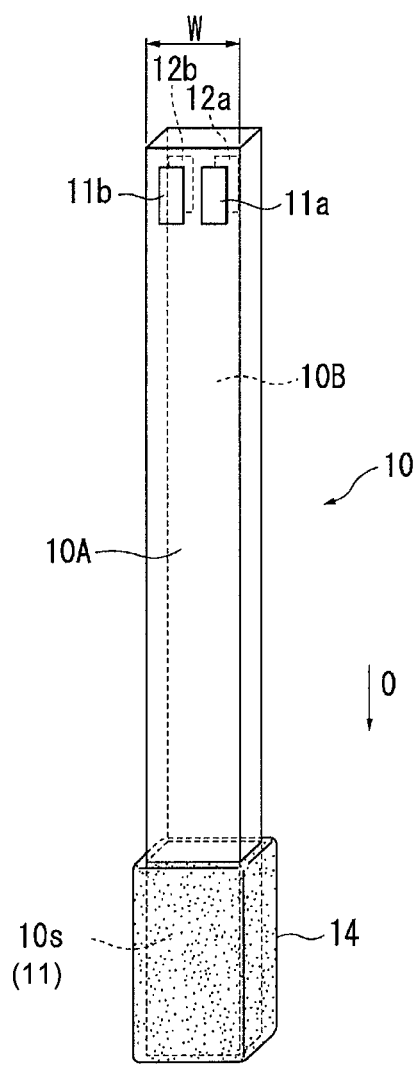
FIG. 9 is a perspective view of a sensing element.

As illustrated in FIG. 9, the sensing element 10 is formed in a plate shape extending in the direction of the axial line O and formed of a gas-detecting portion 11 whose end portion 10s detects oxygen concentration. The gas-detecting portion 10a is coated with the porous protective coat 14. The sensing element 10 itself has a known structure and includes the gas-detecting portion having a solid electrolyte body permeable to oxygen ions and a pair of electrodes, and a heater that heats the gas-detecting portion and that maintains a constant temperature thereof, although this is not illustrated.

The two electrode pads 11a and 11b are arranged in the direction of the width W on the rear-end side of a main surface (front surface) 10A of the sensing element 10. A sensor output signal from the gas-detecting portion is outputted from the electrode pads 11a and 11b via a lead portion (not illustrated). The two electrode pads 12a and 12b are arranged in the width direction on the rear-end side of the other main surface (back surface) 10B that faces the main surface 10A. Power is supplied to the heater via the lead portion (not illustrated).

The electrode pads 11a, 11b, 12a, and 12b are rectangular and elongated in the direction of the axial line O and can be formed as, for example, sintered bodies mainly formed of Pt. According to the present embodiment, the electrode pads 11a and 11b and the electrode pads 12a and 12b that are disposed on the surfaces of the sensing element 10 face and are paired with each other with the sensing element 10 interposed therebetween. Specifically, a pair of the electrode pad 11a and the electrode pad 12a face each other, and another pair of the electrode pad 11b and the electrode pad 12b face each other. In other words, according to the present embodiment, there are two pairs of the electrode pads 11a, 11b, 12a, and 12b.

The four metal terminals 20 (metal terminals 20a, 20b, 20c, and 20d) are held in the insertion holes 90h of the separator 90. The metal terminals 20a and 20c that face each other with the sensing element 10 interposed therebetween and the metal terminals 20b and 20d that face each other with the sensing element 10 interposed therebetween correspond to "pairs of the metal terminals" (see FIG. 4). In other words, according to the present embodiment, there are two pairs of the metal terminals 21a, 20b, 20c, and 20d.

FIG. 3 is a rear view of one of the metal terminals 20. A part of the primary surface 21a that faces the corresponding insertion hole 90h of the first separator 90 (inner circumferential surface of the first separator 90) is a first opposed surface F1. The area of the first opposed surface F1 is denoted by S1 (hatched part in FIG. 3). The lead-wire-connecting portion 23 is exposed to the rear-end side of the first separator 90. The area S1 is an area of the primary surface 21a that is located inside the first separator 90. Accordingly, an area of a part of the primary surface 21a that is adjacent to the lead-wire-connecting portion 23 is excepted from S1.

A part of the secondary surface 22a that faces the corresponding insertion hole 90h (inner circumferential surface of the first separator 90) is a second opposed surface F2. The area of the second opposed surface F2 is denoted by S2 (hatched part in FIG. 3). The area S2 is an area of a part of the secondary surface 22a that is located inside the first separator 90 and that overlaps the elastic portion 22c in the width direction. Accordingly, an area of the joint 22b between the secondary surface 22a and the primary surface 21a is excepted from S2.

The area S1 is larger than the area S2. As illustrated in FIG. 4, at least a part of the second opposed surface F2 is in contact with the insertion hole 90h (inner circumferential surface of the first separator 90), and the first opposed surface F1 is separated from the insertion hole 90h (inner circumferential surface of the first separator 90).

In the case where at least a part of the second opposed surface F2 is in contact with the insertion hole 90h as above, when a reaction force F is applied from the electrode pad 11a of the sensing element 10 outward in the radial direction, the elastic portion 22c facing the second opposed surface F2 can properly withstand the reaction force F. Consequently, the elastic force of the elastic portion 22c is maintained, and the electrode pad 11a and the metal terminal 20 can be electrically connected to each other in a stable manner.

Since the area S2 is smaller than the area S1, the area of the second opposed surface F2, which is likely to be exposed to heat from the first separator 90 because a portion having a part of the area S2 or the entire area S2 is in contact with the insertion hole 90h (inner circumferential surface of the first separator 90) or approaches (the wall surface of) the insertion hole 90h more than the first opposed surface F1, is relatively decreased, and heat transfer from the first separator 90 to the entire metal terminal 20 can be reduced.

Since the first opposed surface F1, which has a large area, is separated from the insertion hole 90h (inner circumferential surface of the first separator 90), the first opposed surface F1, which has an area larger than the area of the second opposed surface F2 and is separated from (the wall surface of) the insertion hole 90h, can be thermally insulated from the first separator 90 with air. Consequently, heat transfer from the first separator 90 to the entire metal terminal 20 can be reduced.

Thus, the elastic portion 22c of the metal terminal 20 is inhibited from being softened and creep-deformed due to heat transfer from the first separator 90, the elasticity thereof is inhibited from decreasing, and the electrode pad 11a of the sensing element 10 and the metal terminal 20 can be electrically connected to each other with certainty.

According to the first embodiment, as illustrated in FIG. 4, the minimum distance d1 between the first opposed surface F1 and the insertion hole 90h (inner circumferential surface of the first separator 90) is longer than the maximum distance d2 between the second opposed surface F2 and the insertion hole 90h (inner circumferential surface of the first separator 90). Thus, the first opposed surface F1, which has an area larger than the area of the second opposed surface F2, is separated from the insertion hole 90h more than the second opposed surface F2 with certainty and can be thermally insulated from the first separator 90 with air. Consequently, heat transfer from the first separator 90 to the entire metal terminal 20 can be further reduced.

According to the first embodiment, as illustrated in FIG. 4, a first stepped portion 90d is formed between a part of the insertion hole 90h of the first separator 90 facing the primary surface 21a and a part thereof facing the secondary surface 22a such that the part facing the primary surface 21a is located nearer than the part facing the secondary surface 22a to the outside in the radial direction.

The secondary surface 22a of the metal terminal 20 is connected to the primary surface 21a with the joint 22b interposed therebetween. The primary surface 21a is located nearer than the secondary surface 22a to the outside in the radial direction. An edge of the primary surface 21a in the width direction engages the first stepped portion 90d to set the position of the metal terminal 20. The joint 22b corresponds to a "second stepped portion" in CLAIMS.

In the case where the part facing the primary surface 21a is thus located nearer than the part facing the secondary surface 22a to the outside in the radial direction, the distance between the insertion hole 90h and the primary surface 21a can be increased, and heat transfer from the first separator 90 to the entire metal terminal 20 can be further reduced by the effect of the above thermal insulation with air. The first stepped portion 90d is also used to set the position of the metal terminal 20. Accordingly, it is not necessary to provide the first separator 90 with a member for positioning of the metal terminals 20, and the shape of the first separator 90 is not complex, which improves productivity.

The joint 22b may be formed in a shape following the first stepped portion 90d, and the joint 22b may engage the first stepped portion 90d to set the position of the metal terminals 20.

A gas sensor according to a second embodiment of the present invention will now be described with reference to FIG. 5 and FIG. 6. The gas sensor according to the second embodiment of the present invention is the same as the gas sensor according to the first embodiment except for a difference in the shape of metal terminals 30, components like to those of the gas sensor according to the first embodiment are designated by like reference numbers, and a description thereof is omitted.

Figure 5:
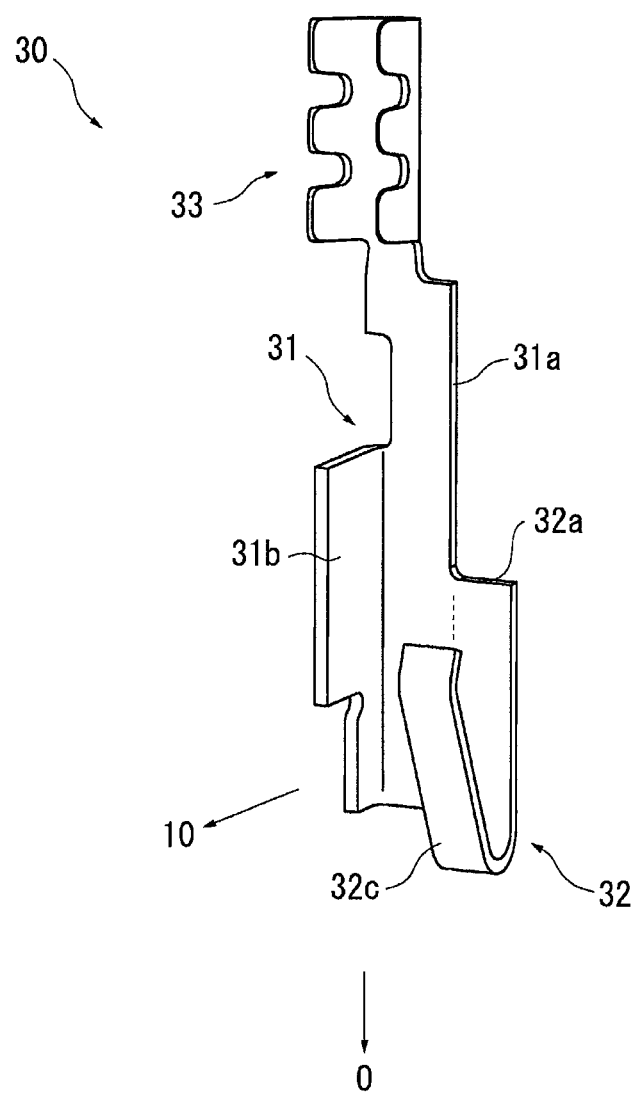
FIG. 5 is a perspective view of one of metal terminals according to a second embodiment of the present invention.
Figure 6:
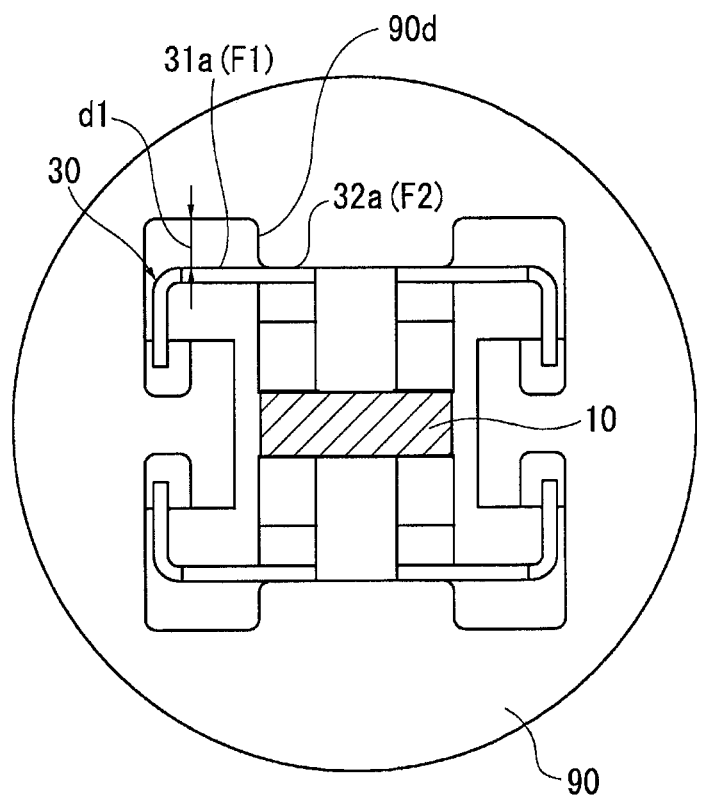
FIG. 6 is a sectional diagram illustrating a state where the metal terminals according to the second embodiment are inserted and held in the insertion holes of the separator.

FIG. 5 is a perspective view of one of the metal terminals 30. FIG. 6 is a sectional diagram illustrating a state where the metal terminals 30 are inserted and held in the insertion holes 90h of the first separator 90. FIG. 6 illustrates the same section as FIG. 4.

As illustrated in FIG. 5, each metal terminal 30 extends in the direction of the axial line O as a whole and includes a lead-wire-connecting portion 33, a main body 31 that is connected to the lead-wire-connecting portion 33 on the front-end side, a protruding piece 32 that protrudes from the front-end side of the main body 31 in a direction intersecting the direction of the axial line O, and an elastic portion 32c that is connected to an end of the protruding piece 32, that is folded toward the sensing element 10, and that is elastically connected to one of the electrode pads, which are integrally formed.

A surface of the main body 31 located opposite the elastic portion 32c is a primary surface 31a. A surface of the protruding piece 32 located opposite the elastic portion 32c is a secondary surface 32a.

The lead-wire-connecting portion 33 is substantially the same as the lead-wire-connecting portion 23 according to the first embodiment. The main body 31 has an L-shaped section and includes a guide portion 31b formed in a manner in which a portion outside the primary surface 31a in the width direction (opposite the secondary surface 32a) is folded at 90 degrees. The lead-wire-connecting portion 33 is connected to the primary surface 31a on the rear-end side.

Another portion outside the primary surface 31a in the width direction (opposite the guide portion 31b) is directly connected to and flush with the secondary surface 32a (without interposing, for example, the joint 22b). The protruding piece 32 includes the elastic portion 32c that is folded from the secondary surface 32a toward the sensing element 10 and that is elastically connected to the electrode pad 11a (see FIG. 1).

The borderline between the primary surface 31a and the secondary surface 32a is illustrated by a dashed line in FIG. 5.

Since the primary surface 31a and the secondary surface 32a are thus flush with each other, in the case where parts of each insertion hole 90h that face these surfaces are flush with each other, it is impossible that at least a part of the second opposed surface F2 is in contact with the insertion hole 90h (inner circumferential surface of the first separator 90) and the first opposed surface F1 is separated from the insertion hole 90h (inner circumferential surface of the first separator 90). In view of this, a part of the insertion hole 90h facing the primary surface 31a is located nearer than a part thereof facing the secondary surface 32a to the outside in the radial direction.

This enables at least a part of the second opposed surface F2 to be in contact with the insertion hole 90h (inner circumferential surface of the first separator 90) and enables the first opposed surface F1 to be separated from the insertion hole 90h (inner circumferential surface of the first separator 90), and heat transfer from the first separator 90 to the entire metal terminals 30 can be reduced. Since the primary surface 31a and the secondary surface 32a are flush with each other, the shape of the metal terminals 30 is not complex, which improves productivity.

In addition, in the case where the primary surface 31a and the secondary surface 32a are flush with each other, the distance between the insertion hole 90h and the primary surface 31a can be longer than that in the case of the first embodiment in which the primary surface 21a is located nearer than the secondary surface 22a to the outside in the radial direction, and heat transfer from the first separator 90 to the entire metal terminals 30 can be further reduced.

A gas sensor according to a third embodiment of the present invention will now be described with reference to FIG. 7 and FIG. 8. The gas sensor according to the third embodiment of the present invention is the same as the gas sensor according to the first embodiment except for a difference in the shape of metal terminals 40 and a first separator 92, components like to those of the gas sensor according to the first embodiment are designated by like reference numbers, and a description thereof is omitted.

Figure 7:
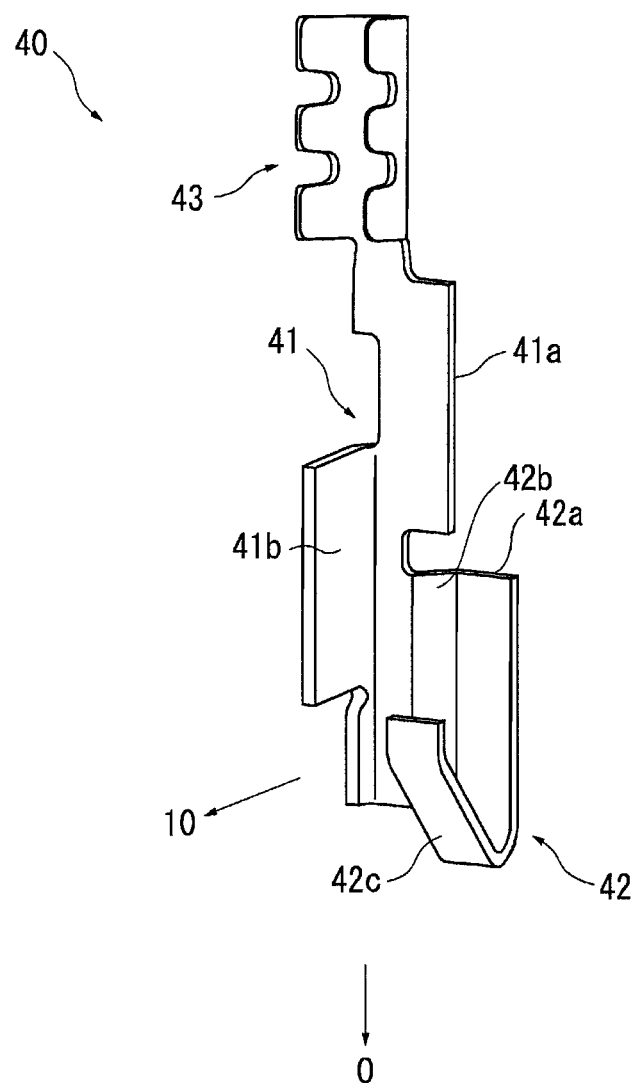
FIG. 7 is a perspective view of one of metal terminals according to a third embodiment of the present invention.
Figure 8:
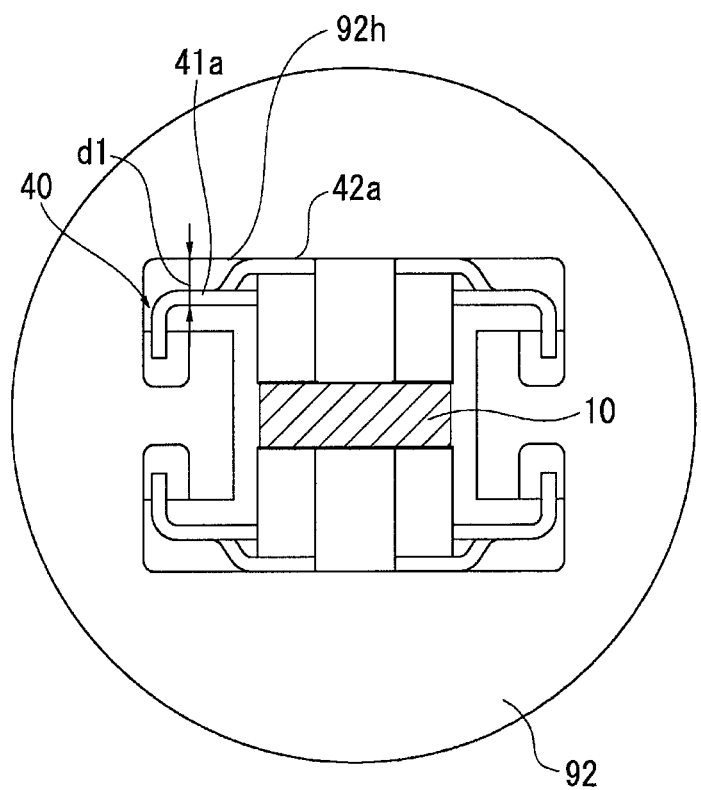
FIG. 8 is a sectional diagram illustrating a state where the metal terminals according to the third embodiment are inserted and held in the insertion holes of the separator.

FIG. 7 is a perspective view of one of the metal terminals 40. FIG. 8 is a sectional diagram illustrating a state where the metal terminals 40 are inserted and held in insertion holes 92h of the first separator 92. FIG. 8 illustrates the same section as FIG. 4.

As illustrated in FIG. 7, each metal terminal 40 extends in the direction of the axial line O as a whole and includes a lead-wire-connecting portion 43, a main body 41 that is connected to the lead-wire-connecting portion 43 on the front-end side, a protruding piece 42 that has a secondary surface 42a connected to a primary surface 41a outside the primary surface 41a in the width direction, and an elastic portion 42c that is connected to an end of the protruding piece 42, that is folded toward the sensing element 10, and that is elastically connected to one of the electrode pads, which are integrally formed.

A surface of the main body 41 located opposite the elastic portion 42c is the primary surface 41a. A surface of the protruding piece 42 located opposite the elastic portion 42c is the secondary surface 42a.

The lead-wire-connecting portion 43 is substantially the same as the lead-wire-connecting portion 23 according to the first embodiment.

The main body 41 has an L-shaped section and includes a guide portion 41b formed in a manner in which a portion outside the primary surface 41a in the width direction (opposite the secondary surface 42a) is folded at 90 degrees. The lead-wire-connecting portion 43 is connected to the primary surface 41a on the rear-end side.

Another portion outside the primary surface 41a in the width direction (opposite the guide portion 41b) is folded in the opposite direction of the guide portion 21b and forms a joint 42b connected to the secondary surface 22a. The secondary surface 22a is parallel to the primary surface 41a. The protruding piece 42 includes the elastic portion 42c that is folded from the secondary surface 42a toward the sensing element 10 and that is elastically connected to the electrode pad 11a (see FIG. 1).

A part of each insertion hole 92h of the first separator 92 facing the primary surface 21a and a part thereof facing the secondary surface 22a are flush with each other.

According to the third embodiment, the primary surface 41a of each metal terminal 40 is located nearer than the secondary surface 42a to the inside in the radial direction, and accordingly, the distance between the insertion hole 92h and the primary surface 41a can be increased, and heat transfer from the first separator 92 to the entire metal terminals 40 can be reduced. Also in the case where parts of the insertion hole 92h of the first separator 92 facing the primary surface 21a and the secondary surface 22a are flush with each other, for example, it is possible that at least a part of the second opposed surface F2 is in contact with the insertion hole 92h (inner circumferential surface of the first separator 92) and the first opposed surface F1 is separated from the insertion hole 92h (inner circumferential surface of the first separator 92). Since the parts of the insertion hole 92h of the first separator 92 facing the primary surface 41a and the secondary surface 42a are flush with each other, the shape of the insertion hole 92h is not complex, which improves productivity.

A method according to a first aspect of an embodiment of the present invention for manufacturing the gas sensor will now be described with reference to FIG. 10 to FIGS. 13A-13D.

Figure 10:
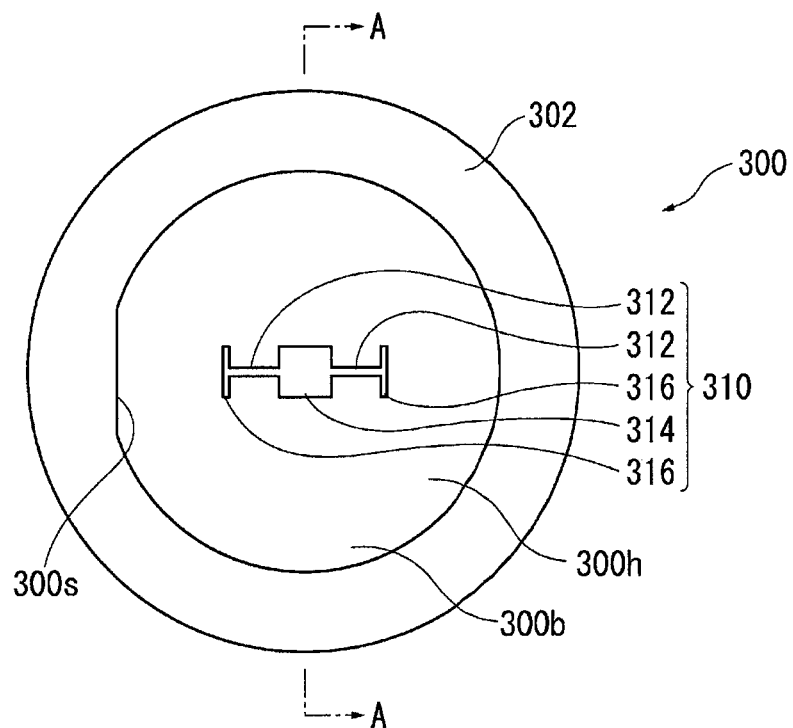
FIG. 10 is a plan view of a first jig used according to a first aspect of an embodiment.
Figure 11:
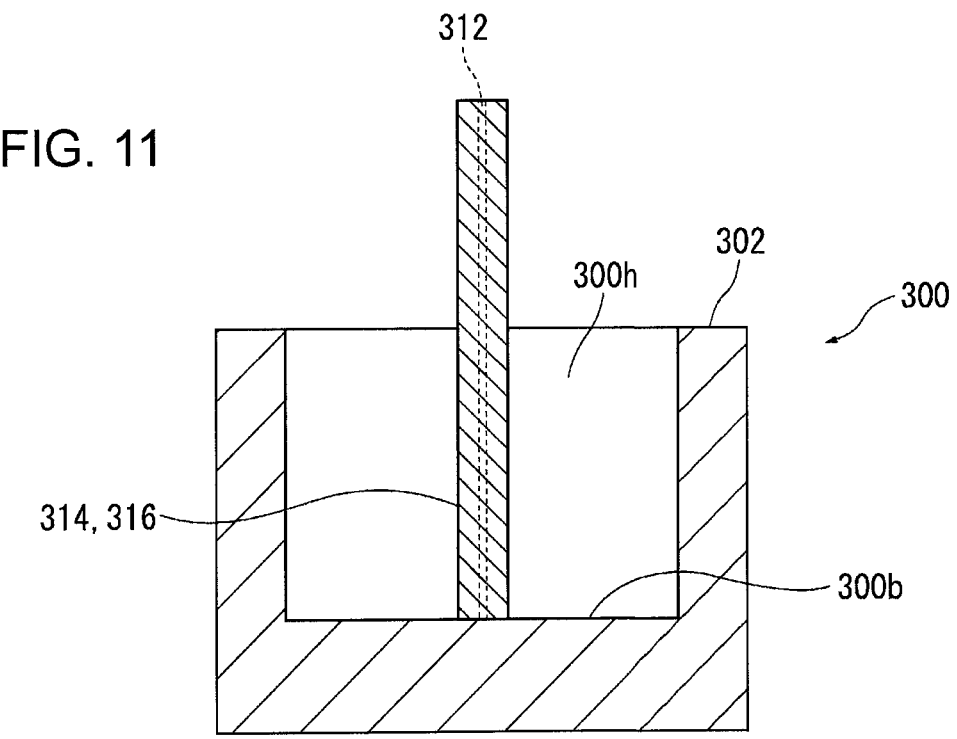
FIG. 11 is a sectional view of FIG. 10 taken along line A-A.
Figure 12:
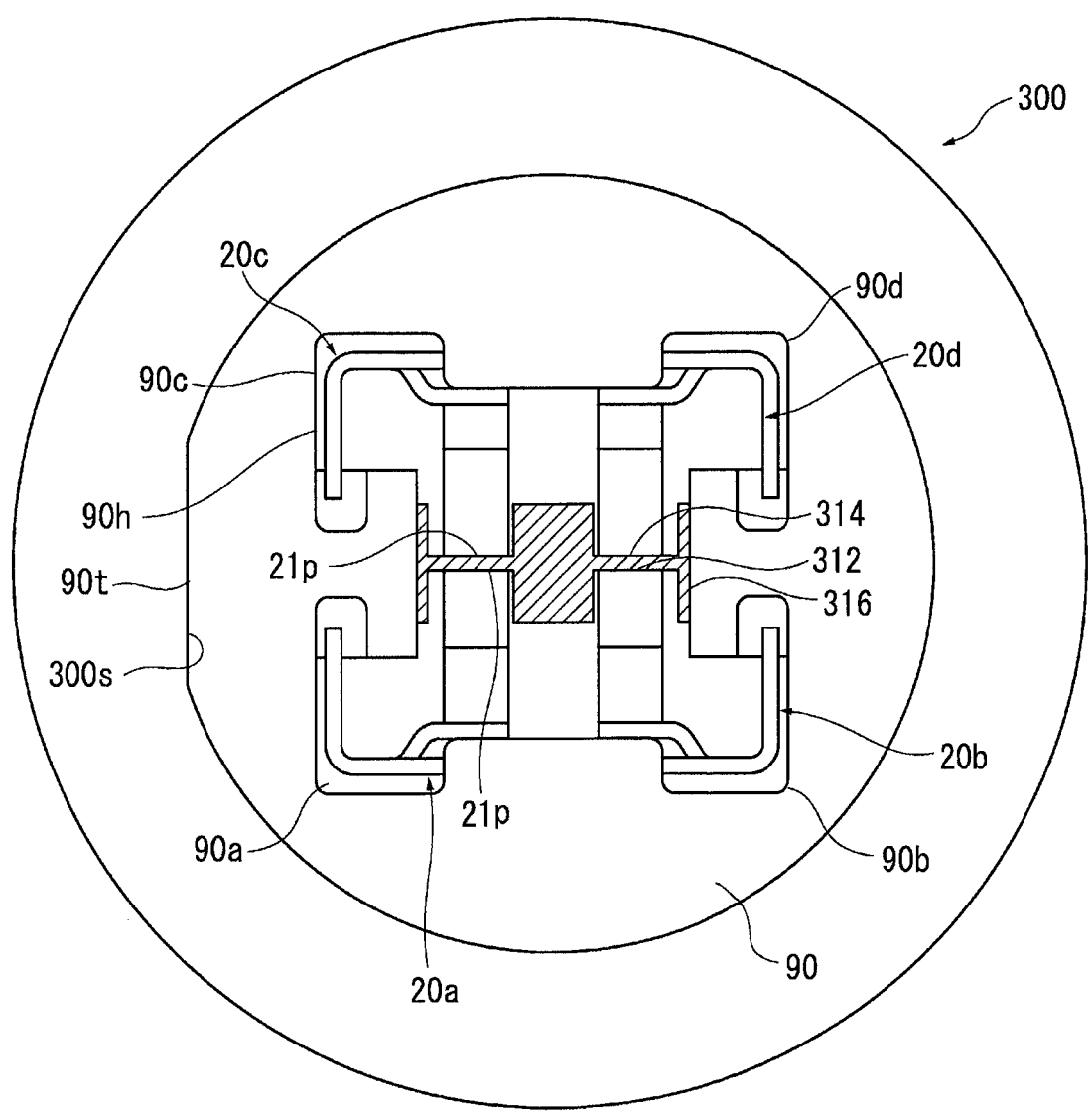
FIG. 12 illustrates a state where the metal terminals are inserted in the separator accommodated in the first jig.

FIG. 10 is a plan view of a first jig 300 used according to the first aspect of the embodiment. FIG. 11 is a sectional view of FIG. 10 taken along line A-A. FIG. 12 illustrates a state where the metal terminals 20a, 20b, 20c, and 20d are inserted in the separator (first separator) 90 accommodated in the first jig 300. FIGS. 13A-13D are process drawings of the method according to the first aspect of the embodiment for manufacturing the gas sensor.

As illustrated in FIG. 10 and FIG. 11, the first jig 300 is formed in a cylindrical shape with a bottom and has, at the center, a cylindrical accommodating space 300h that opens to the upper surface. A protruding portion 310 in the form of a substantially H-shape in a top view protrudes upward from the center of the bottom surface 300b of the accommodating space 300h. The protruding portion 310 is formed at a position corresponding to the insertion hole 90h at the center of the separator 90.

The protruding portion 310 includes a prism portion 314 at the center, two planar portions 312 in a plate shape that extend from opposed surfaces of the prism portion 314 to the opposite directions and that are flush with each other, and two side wall portions 316 that vertically extend from both sides of the planar portions 312 and that each have ends flush with other opposed surfaces of the prism portion 314. The prism portion 314 and the side wall portions 316 protrude from flat surfaces of the planar portions 312. The two planar portions 312 are formed at positions corresponding to the opposed surfaces of a pair of the metal terminals 20a and 20c at the contact portions 21p and the opposed surfaces of the other pair of the metal terminals 20b and 20d at the contact portions 21p (see FIG. 12). The protruding portion 310 protrudes up to a position higher than the upper surface 302 of the first jig 300.

A portion around the accommodating space 300h forms a straight-line portion 300s and prevents rotation of the separator 90 in the circumferential direction, which is described later.

The first jig 300 and the protruding portion 310 can be made of, for example, metal such as stainless steel.

In a metal-terminal holding step of the method according to the first aspect of the embodiment for manufacturing the gas sensor, as illustrated in FIG. 12, the metal terminals 20a, 20b, 20c, and 20d are inserted in four terminal-accommodating holes of the separator 90 accommodated in the first jig 300, which is described in detail later. At this time, the prism portion 314 and the side wall portions 316 come into contact with the side surfaces (surfaces intersecting a surface of each elastic portion 22c) of the metal terminals 20a, 20b, 20c, and 20d and restrict movement of the metal terminals in the width direction, and the metal terminals can be prevented from shifting inside the separator 90 (inside the first jig 300).

The detail of the method according to the first aspect of the embodiment for manufacturing the gas sensor will now be described with reference to FIGS. 13A-13D. FIGS. 13A-13D illustrate a pair of the metal terminals 20b and 20d only. However, the same is true for the other pair of the metal terminals 20a and 20c, which are into the page and concealed in FIGS. 13A-13D.

Figure 13A:
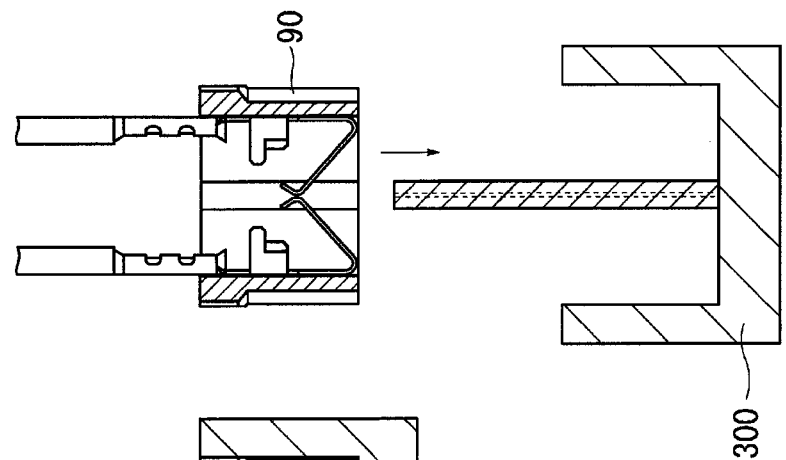
FIGS. 13A-13D are process drawings of a method according to the first aspect of the embodiment for manufacturing the gas sensor.
Figure 13B:
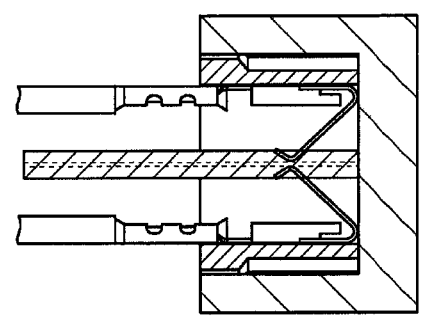

The separator 90 is first moved from the rear-end side (upper side) of the first jig 300 in the direction of the axial line and accommodated, and the planar portions 312 are inserted to positions corresponding to the above opposed surfaces in the insertion holes 90h of the separator 90 (in FIGS. 13A and 13B, a separator accommodating step).

Figure 13C:
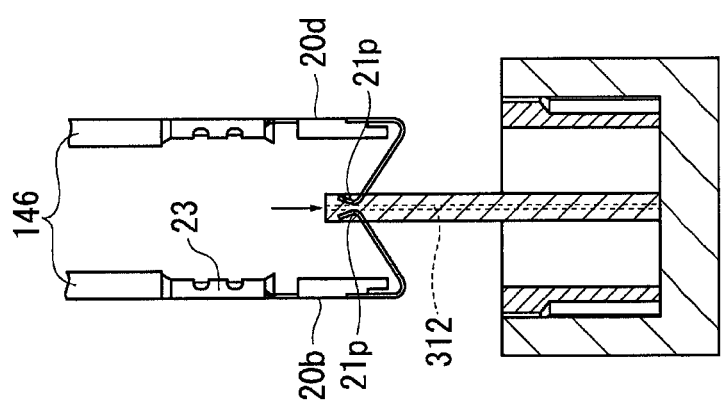

Subsequently, the metal terminals 20b and 20d are inserted into the insertion holes 90h from the rear-end side of the separator 90 such that the planar portions 312 are interposed between the contact portions 21p (the opposed surfaces) and held (in FIGS. 13B and 13C, the metal-terminal holding step). The lead wires 146 are press-fitted to the lead-wire-connecting portions 23 of the metal terminals 20b and 20d in advance.

Figure 13D:
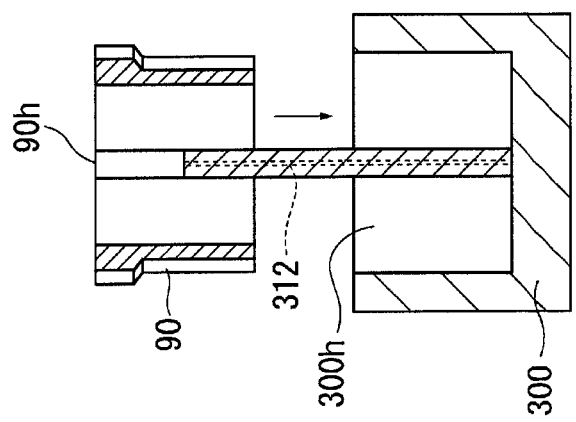

Subsequently, the first jig 300 is relatively removed from the separator 90 to the front-end side (lower side) (in FIG. 13D, a jig removing step).

According to the first aspect of the embodiment, when one or more pairs of the metal terminals 20b and 20d (or 20a and 20c) are thus installed in the separator 90 such that the contact portions 21p face each other, the planar portions 312 of the first jig 300 are interposed between the contact portions 21p. Accordingly, the metal terminals 20b and 20d (or 20a and 20c) that face each other are inhibited from coming into contact and being entangled with each other, the metal terminals are inhibited from being damaged and deformed, and workability can be improved.

According to the present embodiment, when the separator 90 is accommodated in the first jig 300 in the separator accommodating step in FIG. 13B, the planar portions 312 protrude up to positions nearer than the rear end of the separator 90 to the rear-end side. Thus, at the beginning of the subsequent metal-terminal holding step in which the metal terminals 20b and 20d (or 20a and 20c) are inserted into the insertion holes 90h, the metal terminals (contact portions 21p) that face each other are isolated from each other by the planar portions 312, and accordingly, the metal terminals can be inhibited from coming into contact and being entangled with each other with certainty.

According to the present embodiment, as illustrated in FIG. 10 and FIG. 12, the first jig 300 includes the straight-line portion 300s, and the separator 90 includes a second straight-line portion (second restricting member) 90t that engages the straight-line portion 300s. This prevents the separator 90 from rotating in the circumferential direction in the first jig 300 and inhibits the metal terminals from coming into contact and being entangled with each other due to rotation of the separator 90.

According to the present embodiment, the thickness of each planar portion 312 is less than the thickness of the sensing element 10 between the pair of the electrode pads 11a and 12a (or 11b and 12b) on the front and back surfaces. This inhibits the planar portions 312 from causing the metal terminals to plastically deform by increasing the distance between the metal terminals (contact portions 21p) that face each other, and inhibits reliability of the electrical connection from decreasing due to a decrease in the pressure of contact with the electrode pads 11a and 12a (or 11b and 12b) of the sensing element 10, which subsequently occurs.

A method according to a second aspect of the embodiment of the present invention for manufacturing the gas sensor will now be described with reference to FIG. 14 to FIG. 18.

Figure 14:
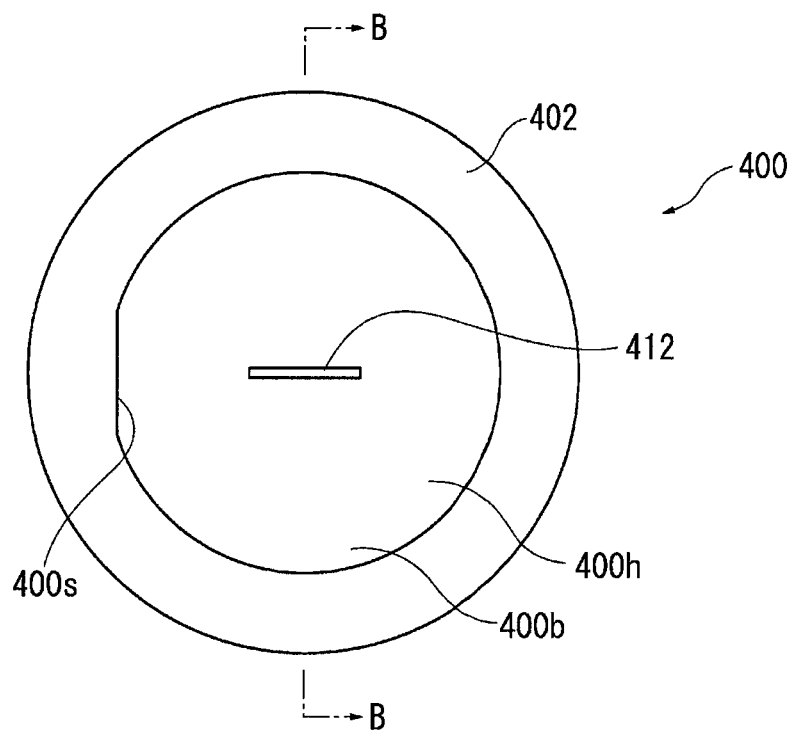
FIG. 14 is a plan view of a second jig used according to a second aspect of the embodiment.
Figure 15:
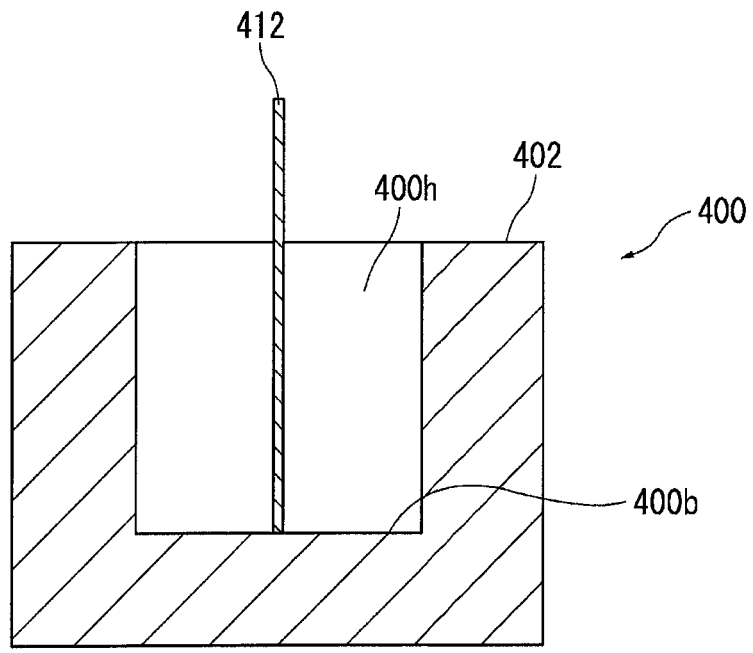
FIG. 15 is a sectional view of FIG. 14 taken along line B-B.
Figure 18:
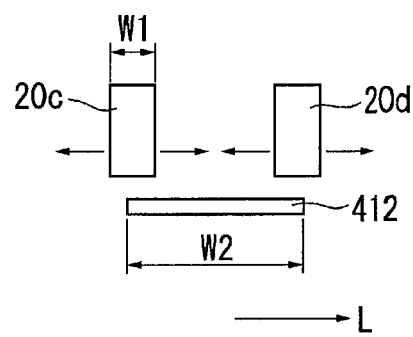
FIG. 18 illustrates a state where the metal terminals shift in arrangement directions with respect to planar portions.
Figure 19:
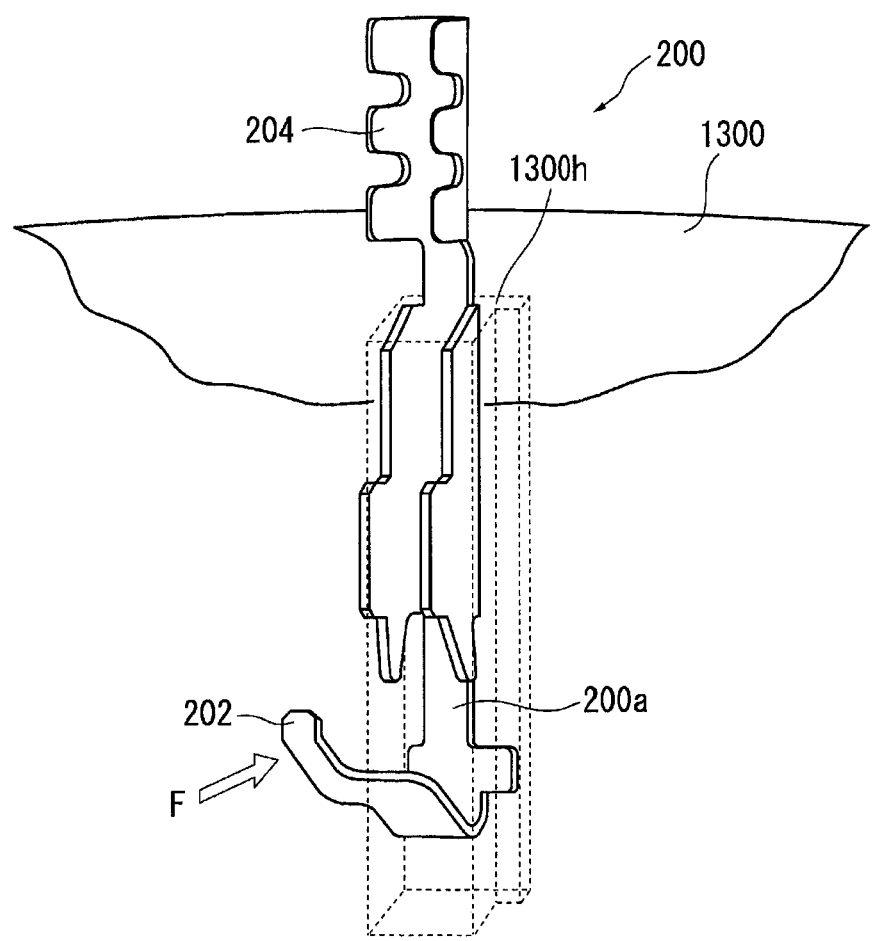
FIG. 19 is a perspective view of a conventional metal terminal.

FIG. 14 is a plan view of a second jig 400 used according to the second aspect of the embodiment. FIG. 15 is a sectional view of FIG. 14 taken along line B-B. FIG. 16 illustrates a state where the metal terminals 20a, 20b, 20c, and 20d are accommodated in the second jig 400. FIGS. 17A-17E are process drawings of the method according to the second aspect of the embodiment for manufacturing the gas sensor. FIG. 18 illustrates a state where the metal terminals 20a to 20d shift in arrangement directions with respect to planar portions 412.

As illustrated in FIG. 14 and FIG. 15, the second jig 400 is formed in a cylindrical shape with a bottom and has, at the center, a cylindrical accommodating space 400h that opens to the upper surface. The two planar portions 412 in a plate shape protrude upward from the center of the bottom surface 400b of the accommodating space 400h. The planar portions 412 are formed at positions corresponding to the insertion hole 90h at the center of the separator 90. The planar portions 412 are formed at positions corresponding to at least the opposed surfaces of a pair of the metal terminals 20a and 20c at the contact portions 21p and the opposed surfaces of the other pair of the metal terminals 20b to 20d at the contact portions 21p (see FIG. 16).

The planar portions 412 protrude up to positions higher than the upper surface 402 of the second jig 400.

A portion around the accommodating space 400h forms a straight-line portion 400s as in the straight-line portion 300s and forms the "first restricting member" that prevents rotation of the separator 90 in the circumferential direction. The separator 90 includes the second straight-line portion (second restricting member) 90t described above.

The second jig 400 and the planar portions 412 can be made of, for example, metal such as stainless steel.

In a metal-terminal holding step of the method according to the second aspect of the embodiment for manufacturing the gas sensor, as illustrated in FIG. 16, the metal terminals 20a, 20b, 20c, and 20d are inserted in the accommodating space 400h of the second jig 400. At this time, the planar portions 412 are inserted between the opposed surfaces of the metal terminals 20a to 20d at the contact portions 21p.

As illustrated in FIG. 16, the metal terminals 20a and 20b are arranged in a direction L along the main surfaces of the planar portions 412, and the metal terminals 20c and 20d are arranged in the same manner on the opposite side with respect to the planar portions 412. The width of the metal terminals 20a to 20d at the contact portions 21p is denoted by W1, and the width of the main surfaces of the planar portions 412 is denoted by W2.

As illustrated in FIG. 18, in the case where the total width (2×W1) in the direction (arrangement direction) L in which the metal terminals 20c and 20d (or 20a and 20b) are arranged is less than W2, even when the metal terminals 20c and 20d shift in the arrangement direction L, the metal terminals 20c and 20d can be inhabited from passing over the planar portions 412 and coming into contact and being entangled with the metal terminals 20a and 20b located on the opposed side with certainty.

As illustrated in a lower part of FIG. 16, in the case where expression 1: GL+GR=W3−W2, GL<W1, and GR<W1 holds where W3 is the maximum width of the insertion holes 90h of the separator 90 in the arrangement direction L, even when the metal terminals 20c and 20d shift in the arrangement direction L, the metal terminals 20c and 20d can be inhabited from passing over the planar portions 412 and coming into contact and being entangled with the metal terminals 20a and 20b located on the opposed side with certainty. The reason is that GL and GR in the expression 1 represent spaces between both sides (the right-hand side and the left-hand side) of the planar portions 412 and the insertion holes 90h, and, when the spaces GL and GR are less than W1, the metal terminals 20c and 20d cannot reach the opposite side with respect to the planar portions 412. The width of the metal terminals 20c and 20d described herein is donated by W1. However, in the case where the widths of the metal terminals are different, it is preferable that the widths of the terminals closest to the spaces GL and GR be less than the spaces GL and GR.

The detail of the method according to the second aspect of the embodiment for manufacturing the gas sensor will now be described with reference to FIGS. 17A-17E. FIGS. 17A-17E illustrate a pair of the metal terminals 20b and 20d only. However, the same is true for the other pair of the metal terminals 20a and 20c, which are into the page and concealed in FIGS. 17A-17E.

The lead wires 146 to be connected to the metal terminals 20b and 20d are inserted into the insertion holes 90h of the separator 90 so as to protrude from the front-end side of the insertion holes 90h (a lead-wire inserting step). Subsequently, the lead-wire-connecting portions 23 of the metal terminals 20b and 20d are press-fitted (electrically connected) to ends of the lead wires 146 (in FIG. 17A, a metal-terminal connecting step).

Subsequently, the metal terminals 20b and 20d are moved from the rear-end side of the second jig 400 and accommodated in the accommodating space 400h at the same positions as the metal terminals 20b and 20d are held in the separator 90, and the planar portions are inserted (interposed) between the contact portions 21p (in FIG. 17B, a metal-terminal accommodating step).

Subsequently, an end of the separator 90 is brought into contact with the rear end (upper surface) 402 of the second jig 400 while the lead wires 146 are pulled toward the rear-end side (in FIG. 17C, a separator contacting step). As illustrated in FIG. 17C, the inner diameter D1 of the accommodating space 400h is smaller than the maximum outer diameter D2 of an end portion of the separator 90.

Subsequently, the metal terminals 20a and 20c are inserted from the front-end side of the insertion holes 90h of the separator 90 in contact with the rear end of the second jig 400 and held in the insertion holes 90h (in FIG. 17D, the metal-terminal holding step).

Subsequently, the second jig 400 is relatively removed from the separator 90 to the front-end side (lower side) (in FIG. 17E, a jig removing step).

According to the second aspect of the embodiment, when one or more pairs of the metal terminals 20a and 20c (or 20b and 20d) are thus installed in the separator 90 such that the contact portions 21p face each other, the planar portions 412 of the second jig 400 are interposed between the contact portions 21p. Accordingly, the metal terminals 20a and 20c (or 20b and 20d) that face each other are inhibited from coming into contact and being entangled with each other, the metal terminals are inhibited from being damaged and deformed, and workability can be improved.

According to the present embodiment, in the separator contacting step in FIG. 17D, the planar portions 412 protrude up to positions nearer than the contact portions to the rear-end side. Thus, when the metal terminals are held in the insertion holes 90h of the separator 90, the metal terminals (contact portions 21p) that face each other are isolated from each other by the planar portions 412, and the metal terminals can be inhibited from coming into contact and being entangled with each other with certainty.

According to the present embodiment, the separator 90 is prevented from rotating in the circumferential direction in the second jig 400 as described above, and the metal terminals can be inhibited from coming into contact and being entangled with each other due to rotation of the separator 90.

It goes without saying that the present invention is not limited to the above embodiments and contains various modifications and equivalents within the spirit and scope of the present invention.

For example, the shape of the metal terminals and the insertion holes of the first separator, for example, is not limited to the above embodiments. Examples of the gas sensor include a NOx sensor in addition to an oxygen sensor and a universal gas sensor.

According to the above embodiments, the lead wires are directly connected to (crimped on) the lead-wire-connecting portions 23 of the metal terminals 20. However, the lead wires are not limited thereto. For example, the lead wires may be directly connected to other components by, for example, crimping, and the other components may be connected to the metal terminals 20 on the rear-end side by being fitted therein. In this case, joints of the metal terminals 20 that are connected to the other components correspond to "lead-wire-connecting portions", and the lead-wire-connecting portions are indirectly connected to the lead wires with the other components interposed therebetween.

The shape of the first jig, the second jig, the separator, and the metal terminals is not limited. The metal terminals may be paired as one pair or two or more pairs.

A pin for positioning may be disposed, as the first restricting member that prevents rotation of the separator in the circumferential direction, on a part of an edge surface of the separator or in the terminal accommodating space of the separator. A plurality of the first restricting members may be provided.

REFERENCE SIGNS LIST 1 gas sensor
10 sensing element
11a, 11b, 12a, 12b electrode pad
20, 30, 40 metal terminal
21, 31, 41 main body
21a, 31a, 41a primary surface
21p contact portion
22, 32, 42 protruding piece
22a, 32a, 42a secondary surface
22b second stepped portion (joint)
22c, 32c, 42c elastic portion
23, 33, 43 lead-wire-connecting portion
90, 92 separator (first separator)
90d first stepped portion
90h, 92h insertion hole (inner circumferential surface of the separator)
90t second restricting member
146 lead wire
300 first jig
300h, 400h accommodating space
300b, 400b bottom surface of the accommodating space
300s, 400s first restricting member
312, 412 planar portion
314, 316 metal-terminal restricting member
400 second jig
O axial line
F1 first opposed surface
F2 second opposed surface
D1 inner diameter of the accommodating space
D2 maximum outer diameter of an end portion of the separator
L arrangement direction

The invention claimed is:

1. A gas sensor, comprising:
a sensing element that is formed in a plate shape extending in a direction of an axial line and that includes an electrode pad on an outer surface of a rear-end side of the sensing element;
a metal terminal that extends in the direction of the axial line and that is electrically connected to the electrode pad;
a tubular separator that has an insertion hole in which the metal terminal is held and that surrounds a part of the sensing element on the rear-end side; and
a lead wire that is connected to a rear-end side of the metal terminal and is pulled out to a rear-end side of the separator, wherein
the metal terminal includes;
a lead-wire-connecting portion that is connected to the lead wire,
a main body that is connected to the lead-wire-connecting portion on a front-end side and that extends in the direction of the axial line,
a protruding piece that protrudes from a front-end side of the main body in a direction intersecting the direction of the axial line,
an elastic portion that is connected to an end of the protruding piece, that is folded toward the sensing element, and that is elastically connected to the electrode pad,
a primary surface that is provided on the main body, located opposite the elastic portion and has a first opposed surface facing the insertion hole, and
a secondary surface that is provided on the protruding piece, located opposite the elastic portion and has a second opposed surface facing the insertion hole,
S1 is larger than S2, where S1 is an area of the first opposed surface and S2 is an area of the second opposed surface,
at least a part of the second opposed surface is in contact with an inner circumferential surface of the separator forming the insertion hole, and
the first opposed surface is separated from the inner circumferential surface of the insertion hole.

2. The gas sensor according to claim 1, wherein a minimum distance d1 between the first opposed surface and the insertion hole, and d2 is longer than a maximum distance d2 between the second opposed surface and the insertion hole.

3. The gas sensor according to claim 1, wherein a part of the insertion hole facing the primary surface is located further out in a radial direction than a part of the insertion hole facing the secondary surface.

4. The gas sensor according to claim 1, wherein the primary surface is located further in, in a radial direction than the secondary surface.

5. The gas sensor according to claim 3, wherein
a first stepped portion is formed between the part of the insertion hole facing the primary surface and the part of the insertion hole facing the secondary surface,
the secondary surface of the metal terminal is connected to the primary surface with a second stepped portion interposed therebetween, and the primary surface is located further out in the radial direction than the secondary surface, and the primary surface or the second stepped portion is configured to position the metal terminal by engaging the first stepped portion.

6. The gas sensor according to claim 1, wherein the secondary surface has a front surface that faces the elastic portion.

7. The gas sensor according to claim 1, wherein the inner circumferential surface of the insertion hole extends in the direction of the axial line and faces the first opposed surface and the second opposed surface.

* * * * *